(12) United States Patent
Tanaka et al.

(10) Patent No.: US 10,898,738 B2
(45) Date of Patent: Jan. 26, 2021

(54) VISUAL FUNCTION PRINTING AGENT, AND METHOD FOR IMPROVING VISUAL FUNCTIONS

(71) Applicants: Megumi Tanaka, Kanagawa (JP); Tsunemaru Tanaka, Kanagawa (JP)

(72) Inventors: Megumi Tanaka, Kanagawa (JP); Tsunemaru Tanaka, Kanagawa (JP)

(*) Notice: Subject to any disclaimer, the term of this patent is extended or adjusted under 35 U.S.C. 154(b) by 0 days.

(21) Appl. No.: 16/332,217

(22) PCT Filed: Sep. 13, 2017

(86) PCT No.: PCT/JP2017/033024
§ 371 (c)(1),
(2) Date: Jun. 24, 2019

(87) PCT Pub. No.: WO2018/052019
PCT Pub. Date: Mar. 22, 2018

(65) Prior Publication Data
US 2020/0009408 A1    Jan. 9, 2020

(30) Foreign Application Priority Data
Sep. 13, 2016 (JP) .................. 2016-178765

(51) Int. Cl.
| | | |
|---|---|---|
| *A61P 27/02* | (2006.01) | |
| *A61K 9/00* | (2006.01) | |
| *A61K 31/706* | (2006.01) | |
| *A61K 31/7084* | (2006.01) | |

(52) U.S. Cl.
CPC ............ *A61P 27/02* (2018.01); *A61K 9/0048* (2013.01); *A61K 31/706* (2013.01); *A61K 31/7084* (2013.01)

(58) Field of Classification Search
CPC .............. A61K 31/7084; A61K 31/706; A61K 9/0048; A61P 27/02
See application file for complete search history.

(56) References Cited

U.S. PATENT DOCUMENTS

| | | | | |
|---|---|---|---|---|
| 6,923,955 B2* | 8/2005 | Till | .................. | A61K 38/063 424/78.04 |
| 7,914,815 B2* | 3/2011 | Till | .................. | A61K 9/0048 424/450 |
| 7,935,332 B2* | 5/2011 | Till | .................. | A61K 38/063 424/78.04 |
| 8,147,816 B2* | 4/2012 | Till | .................. | A61F 9/0008 424/78.04 |
| 8,647,612 B2* | 2/2014 | Garner | .................. | A61K 31/382 424/78.04 |
| 8,697,109 B2* | 4/2014 | Garner | .................. | A61N 5/06 424/423 |
| 8,747,829 B2* | 6/2014 | Till | .................. | A61K 41/00 424/78.04 |
| 9,204,996 B2* | 12/2015 | Till | .................. | A61K 41/00 |
| 9,844,561 B2* | 12/2017 | Imai | .................. | A61P 3/06 |
| 10,258,638 B2* | 4/2019 | Imai | .................. | A61P 27/10 |
| 2016/0287621 A1* | 10/2016 | Sinclair | .................. | C12N 9/80 |

FOREIGN PATENT DOCUMENTS

| | | |
|---|---|---|
| EP | 1755391 A2 | 2/2007 |
| JP | 2008-501343 A | 1/2008 |
| JP | 2008/501343 A | 1/2008 |
| JP | 2008-538215 A | 10/2008 |
| JP | 2008/538215 A | 10/2008 |
| JP | 2008-542296 A | 11/2008 |
| JP | 2008/542296 A | 11/2008 |
| JP | 2018-100222 A | 6/2018 |
| WO | 2014/146044 A1 | 9/2014 |
| WO | 2015/069860 A1 | 5/2015 |
| WO | 2016/171152 A1 | 10/2016 |
| WO | 2016/171282 A1 | 10/2016 |

OTHER PUBLICATIONS

Rajabi-Vardanjani et al., "Designing and Validaiton a Visual; Fatigue Questionaire for Video Disp0lay Terminals Operators," International Journal of Preventive Medicine, 5(7), 841-848 (Jul. 2014).*
ISR; Japan Patent Office; Tokyo, Japan. Oct. 30, 2017; PCT/JP2017/033024.
European Patent Office Search Report; Munich; dated May 12, 2012.

* cited by examiner

*Primary Examiner* — Lawrence E Crane
(74) *Attorney, Agent, or Firm* — Patshegen IP LLC; Moshe Pinchas

(57) ABSTRACT

Provided herein are compositions and methods for improving a visual function, e.g., eyesight, eye strain, blurred vision, dry eye, retinal function, presbyopia, or Visual Display Terminal (VDT) syndrome, that is safe for long-term intake and ensures effective improvement of visual function. The compositions include a nicotinamide mononucleotide (structure shown below) as an active ingredient.

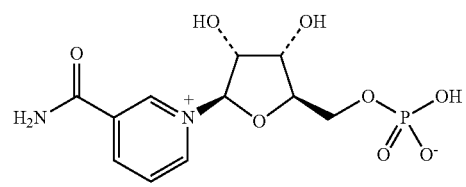

2 Claims, 1 Drawing Sheet

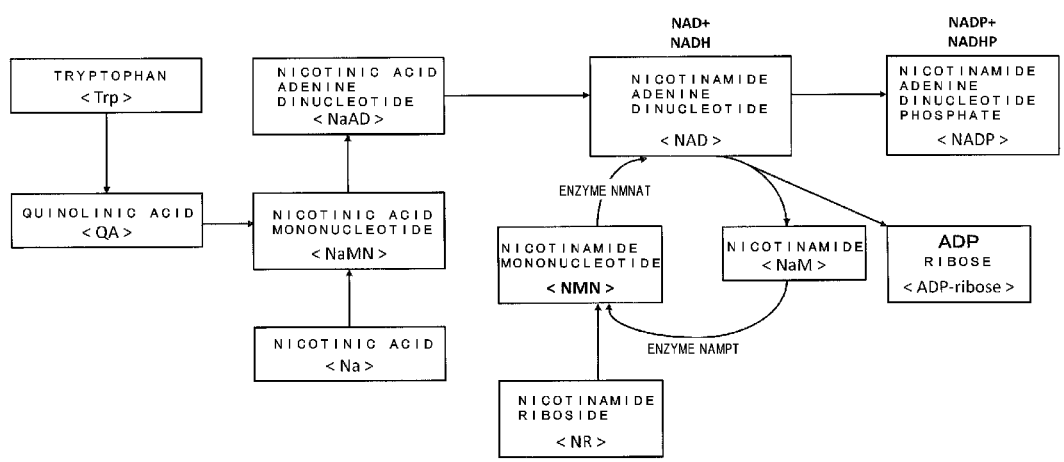

VISUAL FUNCTION PRINTING AGENT, AND METHOD FOR IMPROVING VISUAL FUNCTIONS

The present application is a National Stage entry of International Application No. PCT/JP2017/033024, filed on Sep. 13, 2017.

TECHNICAL FIELD

The present invention relates to a visual function improving agent and a method for improving the visual function.

BACKGROUND ART

Recently, many electronic devices such as a smartphone, a personal computer, a tablet, and an electronic book have become popular, and usage times of them have sharply increased, causing daily heavy burden on eyes of modern people. Especially, a recent study points out that staring small characters and images displayed on a small screen like the smartphone in a short distance is a heavy burden for the eyes. Indoor amusements using eyes, for example, on line games and animations have become popular mainly among young people. "Smartphone-Zombie" meaning the use of the smartphone while walking is daily seen.

A problem of vision loss has become serious for the modern people, especially young people as if it responds to such a circumstance of increase in burden on the eyes. A symptom similar to presbyopia is often seen in a young generation that uses the smartphone for a long time.

Furthermore, recently, excessive stress and disturbance in lifestyle habits often seen in modern life, for example, an irregular lifestyle, an insufficient sleep, a lack of exercise, and an unbalanced diet, also have bad influence on the eyes, thus causing deterioration in visual function.

Technological innovation mainly in microelectronics and information processing rapidly develops information technology (IT), and thus displays (Visual Display Terminals: VDTs) of the personal computer and the like are widely introduced in workplaces. In accordance with this, recently, a new disease referred to as a VDT syndrome attracts attention. This VDT syndrome is a disease that causes troubles on not only the eyes but also a body and a mind due to long time works using the VDTs, thus causing various symptoms in addition to the disorder of the eyes. The symptom includes, for example, eye fatigue, deterioration in eyesight, blurred vision, eye pain, dry eye, shoulder stiffness, pain from neck to shoulders and arms, physical weariness, numbness of hand fingers, backache, headache, giddiness, insomnia, depression, and increased stress. These symptoms are complicatedly caused.

Thus, more and more spread of the smartphone, the personal computer, and the like increases severity of the environment around the eyes of the modern people, and the whole society proceeds to a circumstance where the eyes are excessively used. Furthermore, the excessive stress and the disturbance in lifestyle habits are added to cause the circumstance where it is very difficult for the modern people to maintain the health of the eyes. Then, the deterioration in visual function including deterioration in eyesight caused under such a circumstance is not simply a problem for one person to decline quality of individual life, but a problem that causes troubles on work productivity and operational efficiency. Therefore, it can be said to be a problem for the whole society. Accordingly, it is one of a very important problem in the modern society to take an effective countermeasure to improve the visual function.

While a method for improving the visual function is generally the use of glasses and contact lenses, many people do not like to use them because wearing and maintaining them are burdensome in some cases. Additionally, while various methods of recover training for the eyesight, the presbyopia, and the like have been proposed, they have difficulties in ease of continuation, and it is hard to say that their effects are sufficiently proved.

In improving the visual function, it is an important element to have a nutritious and balanced diet. As nutrients contained in general foods for maintaining the health of visual function, vitamin A, vitamin $B_1$, vitamin $B_2$, vitamin $B_6$, and vitamin C are well known. It is said that vitamin A is effective for protecting a mucous membrane of the eye and maintaining the health of a retina, vitamin $B_1$ is effective for maintaining functions of a nerve and a muscle of the eye, vitamin $B_2$ is effective for promoting regeneration of cells of the eye and protecting the mucous membrane, vitamin $B_6$ is effective for activation of metabolism the cells of the eye, and vitamin C is effective for maintaining transparency of a crystalline lens and preventing congestion. Accordingly, it is important for maintaining the health of the visual function to have a balanced diet containing these nutrients. However, in recent times where the disturbance in eating habits has been pointed out as described above, actually, it is not always easy to daily continue the balanced diet containing the above-described nutrients.

Therefore, recently, many health foods containing ingredients advocating the improvement of the visual function have been commercially available to compensate the shortage of the nutrients for maintaining the health of the eyes. As the ingredients contained in such health foods and contributing to improving the visual function, in addition to anthocyanin, lutein, and docosahexaenoic acid, which recently attract attention, for example, astaxanthin, lycopene, taurine, panthenol, potassium aspartate, chondroitin sulfate, zinc, calcium, and magnesium are known.

Anthocyanin is a glycoside component where among anthocyans as pigment contained in various plants including cassis, blueberry, and the like, anthocyanidin is linked to sugars and sugar chains as aglycon. Anthocyanin is said to have various physiological effects such as an antioxidant action, a lipid improving action, and an antitumor effect. As an exemplary visual function improving agent containing anthocyanin, for example, an axial myopia inhibitor that contains anthocyanin as an active ingredient is disclosed (Patent Document 1).

Lutein is one kind of pigment referred to as carotenoid contained in, for example, green and yellow vegetables such as spinach, carrots, pumpkins, and kale, seaweeds, and egg yolks. It is known that lutein has functions to remove reactive oxygen that causes eye aging and to absorb a harmful blue light emitted from a television, a mobile phone, and the like to protect the eyes. As an exemplary visual function improving agent containing lutein, for example, a visual improvement agent where cassis extract powder and lutein ester are soft capsulated for use is disclosed (Patent Document 2).

Docosahexaenoic acid is a polyunsaturated fatty acid contained much in blue-skinned fish such as a sardine, a horse mackerel, and a saury. Docosahexaenoic acid is produced from eicosapentaenoic acid in body, and said to act to enhance especially the functions of brain and nerve tissues. As an exemplary visual function improving agent containing docosahexaenoic acid, for example, a dynamic visual acuity improving agent that contains docosahexaenoic acid and/or its derivative as an active ingredient is disclosed (Patent Document 3).
Patent Document 1: JP-A-2010-163362
Patent Document 2: JP-A-2003-26589
Patent Document 3: JP-A-10-287563

DISCLOSURE OF THE INVENTION

Problems to be Solved by the Invention

It is an object of the present invention to provide an improving agent and an improving method for a visual function that is safe in long-term intake and ensures effective improvement of the visual function.

Solutions to the Problems

The inventor seriously studied in order to solve the above-described problems, and found that a nicotinamide mononucleotide as an intermediate metabolite involved in biosynthesis of a coenzyme NAD (nicotinamide adenine dinucleotide) has an excellent visual function improving effect. Thus, the present invention was completed.

The present invention is as follows.

[1] A visual function improving agent that contains a nicotinamide mononucleotide as an active ingredient.
[2] The visual function improving agent according to [1] where the improvement of the visual function is an improvement of eyesight, an improvement of eye strain, an improvement of blurred vision, an improvement of dry eye, an improvement of retinal function, an improvement of presbyopia, or an improvement of a VDT syndrome.
[3] The visual function improving agent according to [1] or [2] where the visual function improving agent is a food product for improving the visual function.
[4] The visual function improving agent according to [1] or [2] where the visual function improving agent is a medicinal product for improving the visual function.
[5] A method for improving a visual function that includes causing a target to ingest a nicotinamide mononucleotide by an effective dose, the target needs the nicotinamide mononucleotide by the effective dose (excluding a medical practice to a human).

Effects of the Invention

The present invention ensures the effective improvement of the visual function. The present invention is safe because the nicotinamide mononucleotide as the intermediate metabolite involved in the biosynthesis of in vivo NAD is contained as the active ingredient. The present invention ensures the long-term intake.

BRIEF DESCRIPTION OF THE DRAWINGS

FIG. 1 is an explanatory drawing illustrating a metabolic pathway involved in niacin (generic term of nicotinamide and nicotinic acid).

DESCRIPTION OF PREFERRED EMBODIMENTS

A visual function improving agent according to the present invention contains a nicotinamide mononucleotide as an active ingredient, and provides a visual function improving effect. In the present invention, the improvement of the visual function includes prevention, and stopping and delaying progress of the visual function degradation in addition to the improvement of the visual function in narrow sense. The detailed reason why containing the nicotinamide mononucleotide as the active ingredient provides such an effect is currently examined. However, it is considered to be one reason that the nicotinamide mononucleotide promotes a "sirtuin" typified by NAD+dependent deacetylases Sirt1 and Sirt3, and consequently, metabolism of cells of eyes and cell respiration are activated. The following describes the present invention in detail.

The nicotinamide mononucleotide (chemical formula: $C_{11}H_{15}N_2O_8P$) is a compound produced in bodies of many organisms including human, and expressed with a structural formula [Chem. 1] below. The nicotinamide mononucleotide is generally referred to as NMN, and known as an intermediate metabolite involved in a biosynthesis of coenzyme NAD+.

[Chem. 1]

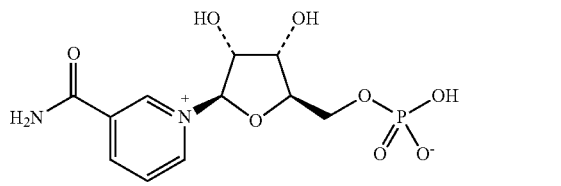

The nicotinamide mononucleotide as the active ingredient of the visual function improving agent is produced in an NAD metabolic pathway by liver tissues, that is, a pathway involved in a synthesis of a nicotinamide adenine dinucleotide (NAD) from a quinolinic acid through a kynurenine pathway, in vivo. This will be specifically described with reference to FIG. 1. FIG. 1 is an explanatory drawing illustrating a metabolic pathway involved in niacin (generic term of a nicotinamide and a nicotinic acid) known as vitamin $B_3$. The nicotinic acid ingested through a meal is absorbed by the liver to be converted into nicotinamide, and the nicotinamide is supplied to the whole body via a blood flow. The cells each absorb the nicotinamide from the blood, and convert it into the NAD and an NADP to use them. The nicotinamide is biosynthesized also from a tryptophan.

As illustrated in FIG. 1, in vivo, when the tryptophan is a starting material, the tryptophan is converted into the quinolinic acid (QA) through the kynurenine pathway as a tryptophan metabolic pathway, and further converted into a nicotinic acid mononucleotide (NaMN). Meanwhile, when the nicotinic acid (Na) is the starting material, the nicotinic acid is directly converted into the NaMN. Afterwards, the NaMN is interconverted into the NAD, a nicotinamide (NaM), and the nicotinamide mononucleotide in a NAD cycle through a nicotinic acid adenine dinucleotide (NaAD). The nicotinamide (NaM) is converted into the nicotinamide mononucleotide by a nicotinamide phosphoribosyltransferase (NAMPT), subsequently, the nicotinamide mononucleotide is converted by a nicotinamide mononucleotide adenyltransferase (NMNAT) to generate the NAD. Note that, the nicotinamide mononucleotide is produced also from a nicotinamide riboside (NR) as an NAD intermediate metabolite.

The nicotinamide mononucleotide includes two types of an α-form and a β-form as optical isomers, and the β-form is used in the present invention. The nicotinamide mononucleotide is obtained by, for example, synthesizing a nicotinamide riboside from the nicotinamide and a ribose (see Bioorg. Med. Chem. Lett., 12, 1135-1137 (2002)), and subsequently, phosphorylating a 5-hydroxyl group of the ribose part (see Chem. Comm, 1999, 729-730). Specifically, for example, first, a reaction solution is prepared by dissolving the nicotinamide and an L-ribose tetraacetate in anhydrous acetonitrile, adding a trimethylsilyl trifluorosulfonic acid by an excessive amount under a nitrogen stream and then stirring at room temperature, and adding methanol to stop the reaction. The above-described reaction solution is poured into a column filled with activated carbon, cleaned with a distilled water, and then eluted with methanol and its product is collected. Next, for a phosphorylation reaction of the 5-hydroxyl group of the L-ribose part of this product, a reaction solution is prepared by dissolving the above-described product in a trimethoxy phosphoric acid, dropping a phosphorus oxychloride below freezing and stirring under the nitrogen stream, adding a sodium hydroxide aqueous solution to neutralize, thus stopping the reaction. A cold acetonitrile-ether solution is added to the above-described reaction solution. Afterwards, a lower layer (water phase) is passed through an anion-exchange resin to collect a reactant, and further purifies the reactant with a cation-exchange resin, thus the high-purity nicotinamide mononucleotide can be collected. The nicotinamide mononucleotide is commercially available from Oriental Yeast Co., ltd. and Bontac Bio-engineering (Shenzhen) Co., Ltd., and those commercial products can be purchased for use.

The nicotinamide mononucleotide is a purified product that contains a few impurities, especially, preferably its purity is 90% or more, and further preferably its purity is 95% or more. When the purity is 90% or less, a bad smell possibly occurs, or the effect of the nicotinamide mononucleotide is possibly reduced to fail to sufficiently provide the effect of the present invention.

While the purity of the nicotinamide mononucleotide is preferably 90% or more as described above, the purity (mass ratio) is defined as a value obtained by subtracting the impurities other than the nicotinamide mononucleotide from 100% in anhydrous terms. Accordingly, the purity of the nicotinamide mononucleotide can be obtained with a formula: nicotinamide mononucleotide purity (%)=100−impurities other than nicotinamide mononucleotide (%). Here, these impurities include, as illustrated in FIG. 1, metabolites excluding the nicotinamide mononucleotide involved in the NAD metabolic pathway, especially, the nicotinamide and the nicotinamide adenine dinucleotide. When the nicotinamide mononucleotide used in the present invention contains a foreign element such as the above-described metabolite involved in the NAD metabolic pathway, for example, the absorption of the nicotinamide mononucleotide into living cells possibly reduces, resulting in the reduction of the effect of the present invention. A quantitative determination of the above-described impurities involved in the NAD metabolic pathway is performed with an absolute calibration curve method using a standard sample where a test solution of dried nicotinamide mononucleotide powder is poured into an HPLC apparatus, and a peak area of an obtained chromatograph is obtained (vertical axis: peak area, horizontal axis: concentration). Since the use of the peak height ensures the quantitative determination with high accuracy in a case of a trace substance, the apparatus to be used is appropriately chosen according to the characteristics of the apparatus. Separated substances are identified based on retention times.

The visual function improving agent according to the present invention is easily manufactured by using the nicotinamide mononucleotide alone or mixing another ingredient. The other ingredient is not specifically limited insofar as the effect of the present invention is provided.

The other ingredient includes, for example, anthocyanin, lutein, docosahexaenoic acid, astaxanthin, lycopene, taurine, panthenol, potassium aspartate, chondroitin sulfate, zinc, calcium, and magnesium, which are known ingredients said to have the visual function improving effect. The other ingredient may include, for example, various kinds of vitamins, a trace element, citric acid, malic acid, a perfume, and an inorganic salt, which are auxiliary ingredients commonly used in the food field.

In the present invention, the other ingredient especially effective in increasing the visual function improving effect includes resveratrol. The resveratrol is known as an antioxidant substance contained in, for example, a grape peel, red wine, a peanut peel, a Japanese knotweed, and a gnetum gnemon. The resveratrol includes trans and cis isomers, a trans/cis isomer mixture, a dimer, and a resveratrol derivative such as methylated resveratrol. The trans isomer stable against heat is usually used for the health food and the like. The resveratrol may be synthetically prepared in addition to one prepared by being extracted from every raw material and purified.

A compounding ratio of the resveratrol and the nicotinamide mononucleotide is not limited. However, from an aspect of extracting the maximum effect of the present invention, the compounding ratio of both is preferably adjusted such that in a daily intake per adult, the resveratrol is 1 to 100 pts.mass while the nicotinamide mononucleotide is 1 to 25 pts.mass.

The visual function improving agent according to the present invention is mainly orally ingested to ensure the improvement of the visual function, especially, the improvement of the eyesight, the improvement of the eye strain, the improvement of the blurred vision, the improvement of the dry eye, the improvement of the retinal function, the improvement of the presbyopia, or the improvement of the VDT syndrome. For the improvement of the eyesight, both eyesights of a static visual acuity and a dynamic visual acuity are set to targets. The eye strain is also referred to as eye fatigue, and has symptoms of full-body fatigue, headache, shoulder stiffness, nausea, and the like in some cases in addition to a tired feeling of eyes, a feeling of oppression, congestion of eyes, and the like. The blurred vision means a symptom where a focus adjustment function of the eye temporarily deteriorates due to overuse of the eyes and the like and the eyesight gets blurred. The dry eye is a disease where discomfort of the eyes and abnormality in the visual function are caused by decrease in amount of tears or decrease in quality of tears. The retinal function is a function where the retina as one component of the eye converts a visual image (optical information) into a neural signal (electrical signal) to transmit the signal to a brain center through an optic nerve. Deterioration of this function possibly causes various retinal diseases such as a floater and a retinal detachment. Accordingly, the improvement of the retinal function leads to the improvement of the retinal disease, and thus the effects on the improvement of the dynamic visual acuity and the improvement of dark adaptation can be expected. The presbyopia means a symptom where the crystalline lens becomes hard with aging and its adjustment function deteriorates, resulting in difficulty in focusing on nearby objects. Recovery of elasticity of the crystalline lens can be expected with the present invention. The VDT syndrome is a disease where the prolonged work using the display (VDT) of the personal computer and the like influences the eyes, the body, and the mind, as described above. Its symptom includes, for example, eye fatigue, deterioration in eyesight, blurred vision, eye pain, dry eye, shoulder stiffness, pain from neck to shoulders and arms, physical weariness, numbness of hand fingers, backache, headache, giddiness, insomnia, depression, and increased stress. These symptoms are complicatedly caused. The present invention reduces the various symptoms.

The method for manufacturing the visual function improving agent is not specifically limited, but a common manufacturing method used for manufacturing it may be appropriately chosen corresponding to its form. For example, when the form is powder, the visual function improving agent can be manufactured by uniformly mixing the nicotinamide mononucleotide and the other ingredient contained as necessary. The nicotinamide mononucleotide as the active ingredient is distributed in the market and commercially available. Especially, for the nicotinamide mononucleotide, a quality management system and a mass production system of the nicotinamide mononucleotide are recently established, supply as a raw material of food composition is allowed, and further, stability as the food composition is confirmed.

The visual function improving agent according to the present invention is usable as a food product and a medicinal product. In the case of the use as the food product, the visual function improving agent can be provided as the food product for improving the visual function in the food field. Daily ingestion in the form of the food product continuously provides the visual function improving effect, thus being especially effective in improving the visual function. The type of the food product as the target of the present invention is not specifically limited, and the target includes a functional food, a food for specified health use, a dietary supplement, a food additive, a feed, a care food, a diet therapy food, a therapeutic diet, a diet food, and similar food product in addition to general food products. Specifically, for example, confectionery (gum, candies, cookies, gummi candies, biscuits, cakes, chocolates, Japanese confectionery, jelly, and the like), bread, noodles, rice/grain processed foods (cereals and the like), meat processed foods, fish and shellfish processed foods, vegetable processed foods, ready-prepared foods, fermented foods, seasonings (source, dressing, ketchup, and the like), spices, dairy products (yogurt, cheese, milk, and the like), ice cream, frozen foods, retort pouch foods, beverages (carbonated beverages, soft drinks, milk-based beverages, alcoholic beverages, sports beverages, fruit-flavored beverages, teas, nutritious beverages, concentrated beverages, and the like), powdered beverages (powdered juice, powdered soup, and the like) are exemplified. The form of the food product is not limited, and especially in the case of the functional food, the food for specified health use, and the like, the food product can be processed to be provided in the form of, for example, a powder, a tablet, a pill, a granule, a hard capsule formulation, a soft capsule formulation, a jelly, a liquid medicine, and a paste medicine.

The intake of the food product is different depending on the type of the food product, age, sex, and weight of a target that takes the food product, the expected effect, and the symptom. However, the daily intake per adult of the nicotinamide mononucleotide contained in the food product is ordinarily 1 mg to 500 mg, preferably 5 mg to 300 mg, and more preferably 50 mg to 300 mg. Less than 1 mg possibly fails to provide the effect of the present invention, while more than 500 mg merely provides almost similar effect but causes economic disadvantage. The compounding ratio of the nicotinamide mononucleotide in the food product can be appropriately set relative to a total food weight in a range of 100% or less.

The food product is safe and side effects are not specifically recognized. Therefore, the food product can be ingested over a long period of time not only to improve the deteriorated visual function but also to prevent the deterioration in visual function. Accordingly, the food product is applicable to not only the target desired to improve the deterioration in visual function but also the healthy target so as not to cause the deterioration in visual function.

Meanwhile, the visual function improving agent according to the present invention can be administered orally or non-orally as a medicinal product (including quasi-drugs) for the improvement of the visual function in the pharmaceutical field. A dosage form of the medicinal product is not specifically limited, but can include, for example, a powder, a tablet, a persistent tablet, a chewable tablet, an effervescent tablet, a troche, a buccal tablet, a sublingual tablet, a capsule formulation, a fine granule, a granule, a pill, a dry syrup, a liquid medicine, a suspending agent, a syrup, a formulation for oral administration such as an elixir, and an eye drop, an eyewash, an eye ointment, an injection preparation, a transfusion, and an external preparation. Among these forms, considering the ease of taking, the stability of the active ingredient, and the like, the formulation for oral administration such as the powder, the tablet, and the capsule formulation is preferable.

The medicinal product can appropriately contain a known additive for formulation, which is adequate for the dosage form and pharmacologically allowed, considering physicochemical property, biological property, and similar property. Such an additive for formulation is exemplified by, for example, an excipient (lactose, starch, crystalline cellulose, sodium phosphate, and the like), a solvent (water, soybean oil, saline solution, a nonaqueous solvent for injection, and the like), a binder (starch, gelatin, gum arabic, sodium alginate, carmellose sodium, methylcellulose, ethyl cellulose, hydroxypropyl methylcellulose, hydroxypropyl cellulose, polyvinylpyrrolidone, and the like), a disintegrant (starch, carmellose sodium, and the like), a lubricant (talc, magnesium stearate, calcium stearate, macrogol, sucrose fatty acid ester, and the like), a coating agent (white sugar, HPC, shellac, gelatin, glycerin, hydroxypropyl methylcellulose, hydroxypropyl methylcellulose phthalate, cellulose acetate phthalate, and the like), a stabilizer (sodium bisulfite, sodium thiosulfate, sodium edetate, sodium citrate, ascorbic acid, dibutylhydroxytoluene, and the like), a preservative (methyl parahydroxybenzoate, ethyl parahydroxybenzoate, propyl parahydroxybenzoate, benzyl alcohol, phenol, chlorobutanol, benzalkonium chloride, benzethonium chloride, sodium dehydroacetate, thimerosal, and the like), a viscous agent (methylcellulose, carmellose sodium, chondroitin sulfate, sodium alginate, and the like), a suspending agent (various nonionic surfactant, methylcellulose, carmellose sodium, and the like), an emulsifier (gum arabic, cholesterol, sorbitan sesquioleate, polysorbate 80, sodium lauryl sulfate, and the like), a buffer (citric acid, acetic acid, sodium phosphate, and boric acid), a surfactant (hydrogenated castor oil, polysorbate 80, and the like), a colorant (water-soluble food pigment, lake pigment, and the like), a corrigent (lactose, white sugar, glucose, mannitol, and the like), a scenting agent (aromatic essential oils), a plasticizer (the phthalic acid esters, vegetable oils, polyethylene glycol, and the like).

A dose of the medicinal product cannot be equally specified because it differs depending on, for example, age, weight, and symptom of the administration target and the number of times of the administration. However, as the dose of the medicinal product, the daily amount per adult of the nicotinamide mononucleotide to be administered is ordinarily 1 mg to 500 mg, preferably 5 mg to 300 mg, and more preferably 50 mg to 300 mg. Less than 1 mg possibly fails to provide the effect of the present invention, while more than 500 mg merely provides almost similar effect but causes economic disadvantage. The compounding ratio of the nicotinamide mononucleotide in the medicinal product can be appropriately set in accordance with the dosage form, the dose of the medicinal product, and the like.

The number of times of the administration of the medicinal product can be appropriately set in accordance with, for example, the age, weight, and symptom of the administration target and the dose per administration of the medicinal product. The number of times of the medicinal product administration per day can be exemplified by once to three times.

Since the nicotinamide mononucleotide has the visual function improving effect as described above, the present invention further provides a method for improving the visual function to cause a target that needs an effective dose of the nicotinamide mononucleotide to ingest it. That is, a method for improving the visual function of the target of the ingestion by causing the target to ingest the visual function improving agent according to the present invention. The target of the ingestion is preferably a mammal such as a human, a mouse, a rat, a rabbit, a dog, a cat, cattle, a horse, a pig, and a monkey, and especially a human is preferable. In the method, the intake of the nicotinamide mononucleotide, the number of intake per day, and similar matters are as described for the visual function improving agent. The visual function improving agent can be ingested anytime in any case, and can be ingested by the target over a long period of time.

Working Example

The following describes the present invention in detail based on the working examples, while the present invention is not limited by these working examples.

Production Example 1

With a usual method, commercially available nicotinamide mononucleotide was uniformly mixed with starch, filled in hard capsules, and capsule formulations containing the nicotinamide mononucleotide of 25 mg and the starch of 320 mg per capsule were manufactured.

Production Example 2

With a usual method, commercially available nicotinamide mononucleotide was uniformly mixed with starch, filled in hard capsules, and capsule formulations containing the nicotinamide mononucleotide of 50 mg and the starch of 292 mg per capsule were manufactured.

Production Example 3

With a usual method, commercially available nicotinamide mononucleotide was uniformly mixed with starch, filled in hard capsules, and capsule formulations containing the nicotinamide mononucleotide of 100 mg and the starch of 195 mg per capsule were manufactured.

Production Example 4

With a usual method, commercially available nicotinamide mononucleotide was uniformly mixed with starch, filled in hard capsules, and capsule formulations containing the nicotinamide mononucleotide of 150 mg and the starch of 145 mg per capsule were manufactured.

Production Example 5

With a usual method, ingredients such as commercially available nicotinamide mononucleotide and resveratrol described in a prescription below were uniformly mixed, filled in hard capsules, and capsule formulations containing the nicotinamide mononucleotide of 5 mg and the resveratrol of 10 mg per capsule were manufactured based on the prescription below.

| Prescription | |
|---|---|
| resveratrol | 10 mg |
| β-nicotinamide mononucleotide | 5 mg |
| pig placenta | 1 mg |
| collagen | 10 mg |
| hyaluronic acid | 0.125 mg |
| elastin | 0.013 mg |
| ceramide | 0.013 mg |
| peucedanum japonicum | 0.125 mg |
| vitamin C | 10 mg |
| amino acid mix | 1.25 mg |
| vitamin mix | 1.25 mg |
| starch | 201.225 mg |
| calcium stearate | 5 mg |
| fine silicon dioxide | 5 mg |
| sum | 250 mg |

Working Example 1

14 subjects (7 males, 7 females, age 39 to 73) with the symptom of eye strain took the capsule formulation manufactured in Production Example 1 by two capsules a day for two months continuously. The subjects performed self-evaluations on the symptom of eye strain with criteria indicated in Table 1 at each of two weeks, one month, and two months after the start of taking. Note that among the subjects, nine persons watched the display of the personal computer and the like for a long time of four to five hours or more a day. Table 1 indicates the result of the evaluated number of people for each criterion.

Working Example 2

Eight subjects (3 males, 5 females, age 48 to 73) with the symptom of blurred vision took the capsule formulation manufactured in Production Example 1 by two capsules a day for two months continuously. The subjects performed self-evaluations on the symptom of blurred vision with criteria indicated in Table 1 at each of two weeks, one month, and two months after the start of taking. Note that among the subjects, four persons watched the display of the personal computer and the like for a long time of four to five hours or more a day. Table 1 indicates the result of the evaluated number of people for each criterion.

Working Example 3

Six subjects (3 males, 3 females, age 48 to 73) with the symptom of dry eye took the capsule formulation manufactured in Production Example 1 by two capsules a day for two months continuously. The subjects performed self-evaluations on the symptom of dry eye with criteria indicated in Table 1 at each of two weeks, one month, and two months after the start of taking. Note that among the subjects, one person watched the display of the personal computer and the like for a long time of four to five hours or more a day. Table 1 indicates the result of the evaluated number of people for each criterion.

Working Example 4

13 subjects (8 males, 5 females, age 39 to 73) took the capsule formulation manufactured in Production Example 1 by two capsules a day for two months continuously. The subjects performed self-evaluations on the eyesight with criteria indicated in Table 1 at each of two weeks, one month, and two months after the start of taking. Note that among the subjects, eight persons watched the display of the personal computer and the like for a long time of four to five hours or more a day. Table 1 indicates the result of the evaluated number of people for each criterion.

Working Example 5

10 subjects (7 males, 3 females, age 48 to 73) with the symptom of presbyopia took the capsule formulation manufactured in Production Example 1 by two capsules a day for two months continuously. The subjects performed self-evaluations on the symptom of presbyopia with criteria indicated in Table 1 at each of two weeks, one month, and two months after the start of taking. Note that among the subjects, five persons watched the display of the personal computer and the like for a long time of four to five hours or more a day. Table 1 indicates the result of the evaluated number of people for each criterion.

Working Example 6

20 subjects (11 males, 9 females, age 38 to 78) with the symptom of eye strain took the capsule formulation manufactured in Production Example 2 by two capsules a day for two months continuously. The subjects performed self-evaluations on the symptom of eye strain with criteria indicated in Table 2 at each of two weeks, one month, and two months after the start of taking. Note that among the subjects, 15 persons watched the display of the personal computer and the like for a long time of four to five hours or more a day. Table 2 indicates the result of the evaluated number of people for each criterion.

Working Example 7

16 subjects (8 males, 8 females, age 38 to 78) with the symptom of blurred vision took the capsule formulation manufactured in Production Example 2 by two capsules a day for two months continuously. The subjects performed self-evaluations on the symptom of blurred vision with criteria indicated in Table 2 at each of two weeks, one month, and two months after the start of taking. Note that among the subjects, 11 persons watched the display of the personal computer and the like for a long time of four to five hours or more a day. Table 2 indicates the result of the evaluated number of people for each criterion.

Working Example 8

13 subjects (7 males, 6 females, age 38 to 78) with the symptom of dry eye took the capsule formulation manufactured in Production Example 2 by two capsules a day for two months continuously. The subjects performed self-evaluations on the symptom of dry eye with criteria indicated in Table 2 at each of two weeks, one month, and two months

TABLE 1

| | | Symptom got worse | Effect was not especially felt | Slightly improved | Improved | Considerably improved |
|---|---|---|---|---|---|---|
| Working Example 1 | Two weeks later | — | 7 | 5 | 1 | 1 |
| | One month later | — | 2 | 7 | 4 | 1 |
| | Two months later | — | — | 8 | 5 | 1 |
| Working Example 2 | Two weeks later | — | 4 | 2 | 2 | — |
| | One month later | — | 2 | 2 | 4 | — |
| | Two months later | — | 1 | 3 | 4 | — |
| Working Example 3 | Two weeks later | — | 3 | 2 | 1 | — |
| | One month later | — | 1 | 3 | 2 | — |
| | Two months later | — | — | 4 | 2 | — |
| Working Example 4 | Two weeks later | — | 9 | 3 | 1 | — |
| | One month later | — | 7 | 4 | 2 | — |
| | Two months later | — | 2 | 7 | 4 | — |
| Working Example 5 | Two weeks later | — | 6 | 4 | — | — |
| | One month later | — | 2 | 6 | 2 | — |
| | Two months later | — | — | 7 | 2 | 1 | after the start of taking. Note that among the subjects, nine persons watched the display of the personal computer and the like for a long time of four to five hours or more a day. Table 2 indicates the result of the evaluated number of people for each criterion.

Working Example 9

21 subjects (12 males, 9 females, age 38 to 78) took the capsule formulation manufactured in Production Example 2 by two capsules a day for two months continuously. The subjects performed self-evaluations on the eyesight with criteria indicated in Table 2 at each of two weeks, one month, and two months after the start of taking. Note that among the subjects, 15 persons watched the display of the personal computer and the like for a long time of four to five hours or more a day. Table 2 indicates the result of the evaluated number of people for each criterion.

Working Example 10

17 subjects (10 males, 7 females, age 43 to 78) with the symptom of presbyopia took the capsule formulation manufactured in Production Example 2 by two capsules a day for two months continuously. The subjects performed self-evaluations on the symptom of presbyopia with criteria indicated in Table 2 at each of two weeks, one month, and two months after the start of taking. Note that among the subjects, 12 persons watched the display of the personal computer and the like for a long time of four to five hours or more a day. Table 2 indicates the result of the evaluated number of people for each criterion.

factured in Production Example 3 by two capsules a day for two months continuously. The subjects performed self-evaluations on the symptom of eye strain with criteria indicated in Table 3 at each of two weeks, one month, and two months after the start of taking. Note that among the subjects, six persons watched the display of the personal computer and the like for a long time of four to five hours or more a day. Table 3 indicates the result of the evaluated number of people for each criterion.

Working Example 12

Eight subjects (3 males, 5 females, age 42 to 79) with the symptom of blurred vision took the capsule formulation manufactured in Production Example 3 by two capsules a day for two months continuously. The subjects performed self-evaluations on the symptom of blurred vision with criteria indicated in Table 3 at each of two weeks, one month, and two months after the start of taking. Note that among the subjects, five persons watched the display of the personal computer and the like for a long time of four to five hours or more a day. Table 3 indicates the result of the evaluated number of people for each criterion.

Working Example 13

Three subjects (1 male, 2 females, age 42 to 63) with the symptom of dry eye took the capsule formulation manufactured in Production Example 3 by two capsules a day for two months continuously. The subjects performed self-evalua-

TABLE 2

| | | Symptom got worse | Effect was not especially felt | Slightly improved | Improved | Considerably improved |
|---|---|---|---|---|---|---|
| Working Example 6 | Two weeks later | — | 6 | 12 | 2 | — |
| | One month later | — | 1 | 13 | 6 | — |
| | Two months later | — | — | 9 | 11 | — |
| Working Example 7 | Two weeks later | — | 8 | 7 | 1 | — |
| | One month later | — | 5 | 8 | 3 | — |
| | Two months later | — | 3 | 9 | 4 | — |
| Working Example 8 | Two weeks later | — | 7 | 5 | 1 | — |
| | One month later | — | 4 | 7 | 2 | — |
| | Two months later | — | 2 | 7 | 4 | — |
| Working Example 9 | Two weeks later | — | 6 | 15 | — | — |
| | One month later | — | 1 | 15 | 5 | — |
| | Two months later | — | 1 | 8 | 12 | — |
| Working Example 10 | Two weeks later | — | 5 | 11 | 1 | — |
| | One month later | — | 3 | 12 | 2 | — |
| | Two months later | — | 1 | 7 | 9 | — |

Working Example 11

Nine subjects (4 males, 5 females, age 42 to 74) with the symptom of eye strain took the capsule formulation manutions on the symptom of dry eye with criteria indicated in Table 3 at each of two weeks, one month, and two months after the start of taking. Note that among the subjects, three persons watched the display of the personal computer and the like for a long time of four to five hours or more a day. Table 3 indicates the result of the evaluated number of people for each criterion.

Working Example 14

11 subjects (4 males, 7 females, age 42 to 84) took the capsule formulation manufactured in Production Example 3 by two capsules a day for two months continuously. The subjects performed self-evaluations on the eyesight with criteria indicated in Table 3 at each of two weeks, one month, and two months after the start of taking. Note that among the subjects, six persons watched the display of the personal computer and the like for a long time of four to five hours or more a day. Table 3 indicates the result of the evaluated number of people for each criterion.

Working Example 15

10 subjects (4 males, 6 females, age 42 to 84) with the symptom of presbyopia took the capsule formulation manufactured in Production Example 3 by two capsules a day for two months continuously. The subjects performed self-evaluations on the symptom of presbyopia with criteria indicated in Table 3 at each of two weeks, one month, and two months after the start of taking. Note that among the subjects, five persons watched the display of the personal computer and the like for a long time of four to five hours or more a day. Table 3 indicates the result of the evaluated number of people for each criterion.

two months after the start of taking. Note that among the subjects, 13 persons watched the display of the personal computer and the like for a long time of four to five hours or more a day. Table 4 indicates the result of the evaluated number of people for each criterion.

Working Example 17

Nine subjects (7 males, 2 females, age 51 to 77) with the symptom of blurred vision took the capsule formulation manufactured in Production Example 4 by two capsules a day for two months continuously. The subjects performed self-evaluations on the symptom of blurred vision with criteria indicated in Table 4 at each of two weeks, one month, and two months after the start of taking. Note that among the subjects, seven persons watched the display of the personal computer and the like for a long time of four to five hours or more a day. Table 4 indicates the result of the evaluated number of people for each criterion.

Working Example 18

Eight subjects (5 males, 3 females, age 42 to 70) with the symptom of dry eye took the capsule formulation manufactured in Production Example 4 by two capsules a day for two months continuously. The subjects performed self-evaluations on the symptom of dry eye with criteria indicated in Table 4 at each of two weeks, one month, and two months after the start of taking. Note that among the subjects, seven persons watched the display of the personal computer and

TABLE 3

| | | Symptom got worse | Effect was not especially felt | Slightly improved | Improved | Considerably improved |
|---|---|---|---|---|---|---|
| Working Example 11 | Two weeks later | — | 1 | 7 | 1 | — |
| | One month later | — | — | 4 | 5 | — |
| | Two months later | — | — | 2 | 7 | — |
| Working Example 12 | Two weeks later | — | 3 | 5 | — | — |
| | One month later | — | 3 | 4 | 1 | — |
| | Two months later | — | 2 | 4 | 2 | — |
| Working Example 13 | Two weeks later | — | 1 | 2 | — | — |
| | One month later | — | 1 | 2 | — | — |
| | Two months later | — | 1 | 2 | — | — |
| Working Example 14 | Two weeks later | — | — | 11 | — | — |
| | One month later | — | — | 4 | 7 | — |
| | Two months later | — | — | 1 | 8 | 2 |
| Working Example 15 | Two weeks later | — | — | 10 | — | — |
| | One month later | — | — | 5 | 5 | — |
| | Two months later | — | — | 1 | 9 | — |

Working Example 16

17 subjects (12 males, 5 females, age 42 to 77) with the symptom of eye strain took the capsule formulation manufactured in Production Example 4 by two capsules a day for two months continuously. The subjects performed self-evaluations on the symptom of eye strain with criteria indicated in Table 4 at each of two weeks, one month, and the like for a long time of four to five hours or more a day. Table 4 indicates the result of the evaluated number of people for each criterion.

Working Example 19

18 subjects (13 males, 5 females, age 42 to 82) took the capsule formulation manufactured in Production Example 4 by two capsules a day for two months continuously. The subjects performed self-evaluations on the eyesight with criteria indicated in Table 4 at each of two weeks, one month, and two months after the start of taking. Note that among the subjects, 13 persons watched the display of the personal computer and the like for a long time of four to five hours or more a day. Table 4 indicates the result of the evaluated number of people for each criterion.

Working Example 20

14 subjects (11 males, 3 females, age 48 to 82) with the symptom of presbyopia took the capsule formulation manufactured in Production Example 4 by two capsules a day for two months continuously. The subjects performed self-evaluations on the symptom of presbyopia with criteria indicated in Table 4 at each of two weeks, one month, and two months after the start of taking. Note that among the subjects, nine persons watched the display of the personal computer and the like for a long time of four to five hours or more a day. Table 4 indicates the result of the evaluated number of people for each criterion.

Working Example 22

Four subjects (2 males, 2 females, age 48 to 68) with the symptom of blurred vision took the capsule formulation manufactured in Production Example 5 by two capsules a day for two months continuously. The subjects performed self-evaluations on the symptom of blurred vision with criteria indicated in Table 5 at each of two weeks, one month, and two months after the start of taking. Note that among the subjects, three persons watched the display of the personal computer and the like for a long time of four to five hours or more a day. Table 5 indicates the result of the evaluated number of people for each criterion.

Working Example 23

Five subjects (3 males, 2 females, age 38 to 68) took the capsule formulation manufactured in Production Example 5 by two capsules a day for two months continuously. The subjects performed self-evaluations on the eyesight with criteria indicated in Table 5 at each of two weeks, one month, and two months after the start of taking. Note that among the subjects, four persons watched the display of the

TABLE 4

| | | Symptom got worse | Effect was not especially felt | Slightly improved | Improved | Considerably improved |
|---|---|---|---|---|---|---|
| Working Example 16 | Two weeks later | — | — | 11 | 6 | — |
| | One month later | — | — | — | 16 | 1 |
| | Two months later | — | — | — | 13 | 4 |
| Working Example 17 | Two weeks later | — | 1 | 7 | 1 | — |
| | One month later | — | — | 3 | 6 | — |
| | Two months later | — | — | 2 | 6 | 1 |
| Working Example 18 | Two weeks later | — | 1 | 6 | 1 | — |
| | One month later | — | — | 5 | 3 | — |
| | Two months later | — | — | 3 | 5 | — |
| Working Example 19 | Two weeks later | — | — | 14 | 4 | — |
| | One month later | — | — | 4 | 13 | 1 |
| | Two months later | — | — | 1 | 14 | 3 |
| Working Example 20 | Two weeks later | — | — | 12 | 2 | — |
| | One month later | — | — | 4 | 10 | — |
| | Two months later | — | — | 2 | 11 | 1 |

Working Example 21

Five subjects (3 males, 2 females, age 38 to 68) with the symptom of eye strain took the capsule formulation manufactured in Production Example 5 by two capsules a day for two months continuously. The subjects performed self-evaluations on the symptom of eye strain with criteria indicated in Table 5 at each of two weeks, one month, and two months after the start of taking. Note that among the subjects, four persons watched the display of the personal computer and the like for a long time of four to five hours or more a day. Table 5 indicates the result of the evaluated number of people for each criterion.

personal computer and the like for a long time of four to five hours or more a day. Table 5 indicates the result of the evaluated number of people for each criterion.

Working Example 24

3 subjects (2 males, 1 female, age 48 to 68) with the symptom of presbyopia took the capsule formulation manufactured in Production Example 5 by two capsules a day for two months continuously. The subjects performed self-evaluations on the symptom of presbyopia with criteria indicated in Table 5 at each of two weeks, one month, and two months after the start of taking. Note that among the subjects, two persons watched the display of the personal computer and the like for a long time of four to five hours or more a day. Table 5 indicates the result of the evaluated number of people for each criterion.

TABLE 5

|  |  | Symptom got worse | Effect was not especially felt | Slightly improved | Improved | Considerably improved |
|---|---|---|---|---|---|---|
| Working Example 21 | Two weeks later | — | 2 | 3 | — | — |
|  | One month later | — | — | 5 | — | — |
|  | Two months later | — | — | 5 | — | — |
| Working Example 22 | Two weeks later | — | 3 | 1 | — | — |
|  | One month later | — | 3 | 1 | — | — |
|  | Two months later | — | 1 | 3 | — | — |
| Working Example 23 | Two weeks later | — | 3 | 2 | — | — |
|  | One month later | — | 1 | 2 | 3 | — |
|  | Two months later | — | — | 4 | 1 | — |
| Working Example 24 | Two weeks later | — | 2 | — | 1 | — |
|  | One month later | — | — | 2 | 1 | — |
|  | Two months later | — | — | 2 | 1 | — |

As seen from the above-described results, the proportion of the subjects provided with the improving effect of the visual function ("slightly improved," "improved," and "considerably improved") by taking the visual function improving agent of the present invention was considerably high, and this was observed to ensure the improving effect of the visual function by the visual function improving agent of the present invention.

The invention claimed is:

1. A method for improving eye strain, comprising causing a host in need thereof to ingest a nicotinamide mononucleotide by an effective dose, the host needing the nicotinamide mononucleotide by the effective dose.

2. A method for improving eye strain according to claim 1, wherein the eye strain that is improved is associated with Visual Display Terminal (VDT) syndrome.

* * * * *